United States Patent [19]

Bishop et al.

[11] Patent Number: 5,210,702
[45] Date of Patent: May 11, 1993

[54] APPARATUS FOR REMOTE ANALYSIS OF VEHICLE EMISSIONS

[75] Inventors: Gary Bishop, Louisville; Donald H. Stedman, Englewood, both of Colo.

[73] Assignee: Colorado Seminary, Denver, Colo.

[21] Appl. No.: 633,952

[22] Filed: Dec. 26, 1990

[51] Int. Cl.[5] .............................................. G01N 21/00
[52] U.S. Cl. ................................. 364/496; 250/338.5; 250/339; 250/372; 364/497
[58] Field of Search ....................... 250/338.5, 339, 372; 364/496, 497, 498

[56] References Cited

U.S. PATENT DOCUMENTS 4,924,095 5/1990 Swanson, Jr. ................ 250/338.1 X

OTHER PUBLICATIONS

Bishop; Gary A., "IR Long-Path Photometry: A Remote Sensing Tool for Automobile Emission", 1989, American Chemical Society.
Chaney; Lucian W., "The Remote Measurement of Traffic Generated Carbon Monoxide", Mar., 1983, Journal of the Air Pollution Control Association, pp. 220-222.
Stedman; Donald, "Automobile carbon monoxide emission" 1989, Environmental Science & Technology, pp. 147-149.

Primary Examiner—Parshotam S. Lall
Assistant Examiner—Edward R. Cosimano
Attorney, Agent, or Firm—Dorr, Carson, Sloan & Peterson

[57] ABSTRACT

A gas analysis device for the remote detecting, measuring and recording of $NO_x$, CO, $CO_2$, HC and $H_2O$ levels from the exhaust of moving motor vehicles. It utilizes a source of collimated infrared and ultraviolet radiation and includes a mechanism for receiving and measuring the infrared and ultraviolet radiation from its source, and another mechanism for measuring background infrared and ultraviolet radiation levels in the ambient atmosphere. The receiving mechanism splits the combined infrared and ultraviolet radiation into separate infrared and ultraviolet beams. A mechanism receives the separate ultraviolet beam and generates a signal indicative of $NO_x$. Another mechanism splits the infrared beam into two to four components, and devices are positioned for receiving each of the infrared components and generating two to four signals indicative of, for example, CO, $CO_2$, HC and $H_2O$. Another associated mechanism then computes and produces signals indicative of the amount of CO, $CO_2$, HC, $NO_x$ and $H_2O$ in the path of the infrared and ultraviolet radiation from the source, thereby making it capable of measuring emissions of vehicles. The source and the receiving mechanism are aligned on opposite sides of a roadway, both being at the elevation of the to-be-measured vehicle exhaust. Vehicles traveling on that roadway and passing through the radiation emanating from the source interrupt reception of the beam by the detector, thereby initiating a detection sequence. In one embodiment a visual recording device is positioned for visually recording the vehicle and test results.

18 Claims, 2 Drawing Sheets

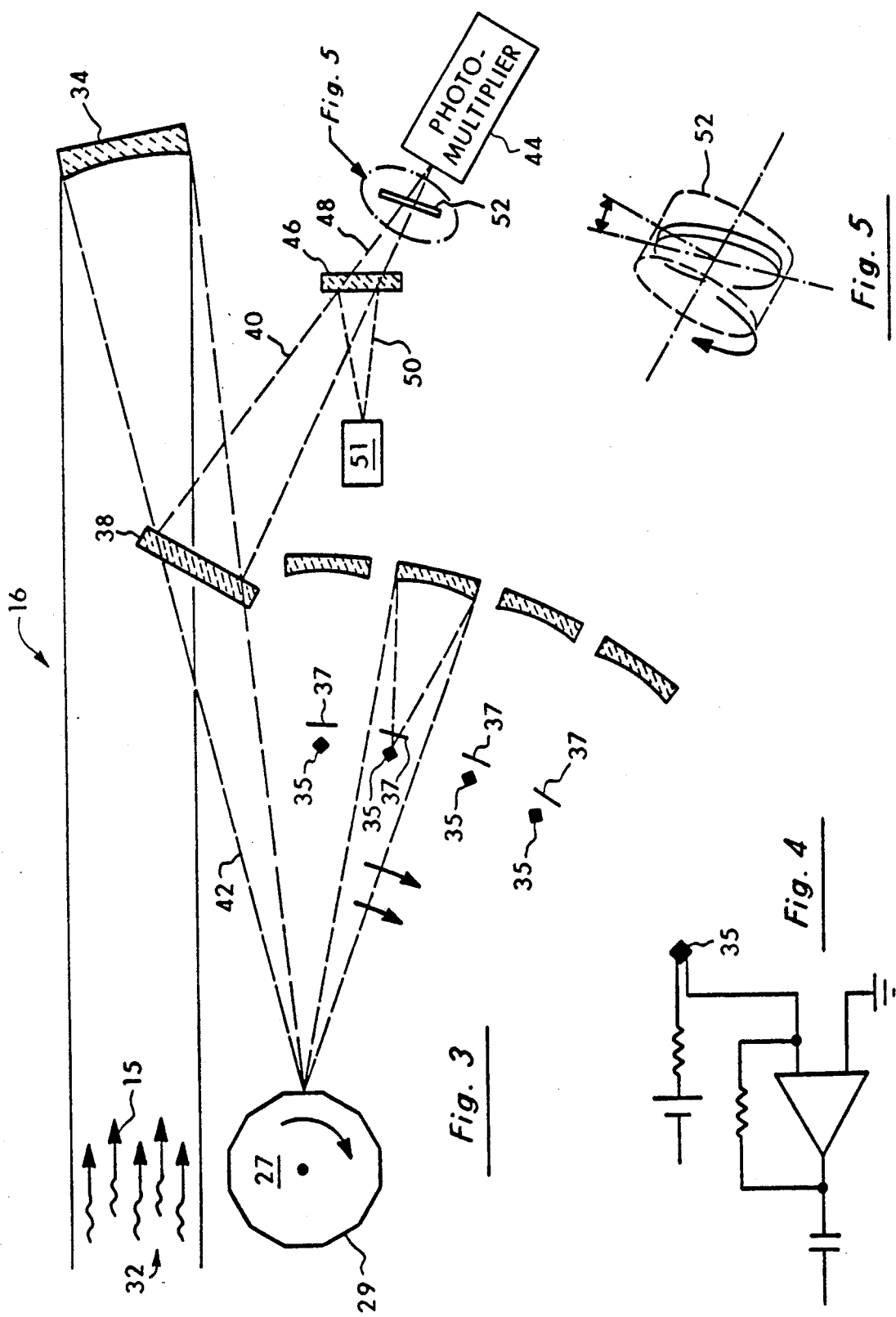

APPARATUS FOR REMOTE ANALYSIS OF VEHICLE EMISSIONS

BACKGROUND OF THE INVENTION

Federal and state governments, along with vehicle manufacturers, test and certify new vehicle emissions, and also carry out some in-use testing of older vehicles. These tests comply with the Federal Test Procedure (FTP) as outlined in the Federal Register, which is a carefully designed and specified three phase test under "cold transient," "cold stabilized," and "hot transient" conditions. The vehicle is generally driven in a series of accelerations, decelerations, stops and starts on a chassis dynamometer, whose inertia and friction are specifically set for each vehicle. The emissions from each phase are collected at a constant volume into a sample bag, and the concentrations of each species of pollutant are determined from the integration of the entire bag with a final result given in grams of pollutant per mile.

The driving course is modeled after a "typical" summertime commute to work in Los Angeles. Each of these tests takes at least twelve hours to complete and costs in excess of about $700, in 1990 dollars. The reproducibility of the results for a given vehicle is claimed to be plus or minus 20%, controlled mainly by the repeatability of the vehicle emissions system and not by the test system or gas analysis protocols. Presently available computer models are based on the concept that the FTP emissions measured from a fleet of vehicles is well-correlated, though not necessarily one to one, with the emissions which the same fleet would exhibit under in-use driving conditions. However, since very little is known about actual on the road fleet emissions, it is impossible to truly gauge the accuracy of this assumption.

In addition to any new car emission certification programs, there are also state inspection and maintenance (IM) programs which are designed to test every vehicle in a given area and are, therefore, much less rigorous tests. The most sophisticated centralized IM testing programs use a chassis dynamometer with one or two fixed loads and speeds and measure the steady-state emissions as a percent of the exhaust. Many centralized, and all decentralized, programs measure only idle emissions as a percent of the exhaust at one, and possibly two, engine speeds. In late 1986, a fuel efficient automobile test (FEAT) system was developed and designed to remotely detect carbon monoxide and carbon dioxide levels in vehicular emissions and to make specific measurements on individual vehicles. This system is more specifically described in an article entitled, *"Automobile Carbon Monoxide Emission"*, Environmental Science Technology, Volume 23, pages 147–149, 1989. Also see *"IR Long-Path Photometry: A Remote Sensing Tool For Automobile Emissions,"* Analytical Chem., Volume 61, pages 671A–676A, 1989. This particular device, while extremely accurate, had its limitations in that it was unable to identify the specific vehicles which was found to be emitting carbon monoxide which was in excess of acceptable levels so that the vehicle owner could be subsequently contacted and advised to adjust or repair or modify the vehicle to control its emissions. In response to the need to identify vehicles, U.S. patent application Ser. No. 470,917, was prepared and filed on Jan. 26, 1990, by the inventors of the present application, and which application is assigned to the same assignee as the present application, the contents of which application are specifically incorporated herein by reference. Moreover, while it was capable of measuring carbon monoxide and carbon dioxide, it was not capable of measuring other emission components or the temperature at which the vehicle was operating, the knowledge of which would be extremely valuable to have.

As indicated, it is known to the inventors that the basic idea of remotely measuring vehicle emissions is not a new one. Lockheed Missiles and Space Corporation first attempted construction of an across the road monitor, the successful operation of which was never published. L. Chaney *"The Remote Measurement of Traffic Generated Carbon Monoxide,"* J. Air Pollution Control Association, Vol. 33, pages 220–222, 1983, proved that carbon monoxide fumes (and only carbon monoxide) from passing vehicles could be observed in real-time using a gas filter correlation radiometer. However, Chaney's system did not include any of the parameters required to accurately measure emissions data from vehicle exhaust plume observations.

It is therefore seen that it would be of particular interest to measure the hydrocarbon as well as nitrogen oxide and water emission levels of identifiable individual vehicles. Therefore, there is still a need for a remote sensing and measuring device to permit measurement of vehicle exhaust while the vehicles are in use. This technique or device permits the quantification of not only carbon monoxide, but also carbon dioxide, hydrocarbon, nitrogen oxide, and water vapor emissions, as well as providing the option of identifying each individual vehicle being tested by the device.

SUMMARY OF THE INVENTION

In view of the foregoing, it is one object of the present invention to provide an improved remote gas analysis device the detection of emission levels of all polluting components in vehicle exhaust.

It is another object of the present invention to provide an emissions detection device specifically designed to detect carbon monoxide, carbon dioxide, hydrocarbon and nitrogen oxide simultaneously in the emissions of vehicles.

It is yet another object of the present invention to provide an emissions detection device specifically designed to also simultaneously measure the operating temperature of vehicles while also measuring the amount of specific pollutants from that vehicle.

Another object of the present invention is to provide such a device which remotely detects and measures carbon monoxide, carbon dioxide, hydrocarbon and nitrogen oxide emissions from in-use vehicles.

A further object of the present invention is to provide such a remote detection device which includes visual monitoring and recording capabilities so as to identify specific vehicle both on-line and in recorded form from which specific carbon monoxide, carbon dioxide, hydrocarbon, and nitrogen oxide emission levels at a specific temperature are being generated.

The foregoing objects and advantages of the present invention are obtained by providing a gas analysis device for detecting and measuring changes in carbon monoxide, carbon dioxide, hydrocarbon, nitrogen oxide and water vapor levels in the ambient atmosphere by utilizing both collimated infrared and ultraviolet radiation passing through the ambient atmosphere. The device includes a mechanism adapted to receive and measure the infrared and ultraviolet radiation and a device for measuring background infrared and ultraviolet radiation levels in the ambient atmosphere. A device splits the combined infrared and ultraviolet radiation which is received from the atmosphere into separate infrared and ultraviolet beams.

Another mechanism is provided for splitting the separate infrared beam into at least two and preferably three or four separate infrared beam components, and devices are positioned for receiving each of the infrared beam components and generating second, third and preferably fourth and fifth electrical signals indicative of the absorption of the infrared beam radiation in the ambient atmosphere by carbon monoxide (CO), carbon dioxide ($CO_2$) and also preferably by hydrocarbons (HC generally) and water ($H_2O$). Yet another mechanism is provided for receiving the separate ultraviolet beam and generating a first electrical signal indicative of the absorption of the ultraviolet radiation by nitrogen oxides ($NO_x$ generally, such as NO, $NO_2$ and the like) in the ambient atmosphere. Then, in the preferred embodiments, a mechanism is provided which is responsive to the electrical signals for computing and for producing output signals indicative of the amount of CO, $CO_2$, HC, $NO_x$ and $H_2O$ in the path of the collimated infrared and ultraviolet radiation in the ambient atmosphere, thereby making it capable of measuring emissions of vehicles passing through the ambient atmosphere. Beam splitting of the infrared radiation from the ultraviolet radiation may be accomplished using a prism, a dichroic mirror, or any other mechanism which is capable of splitting the received infrared radiation from the received ultraviolet radiation.

These and other objects of the present invention will become apparent to those skilled in the art from the following detailed description, showing the contemplated novel construction, combination, and elements herein described, and more particularly defined by the appended claims. It being understood changes in the precise embodiment of the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention and the best modes presently devised for the practical application of the principles thereof, in which:

FIG. 3 is a schematic diagram of one preferred embodiment of a light detector system for use in the remote measuring and monitoring system of the present invention;

FIG. 4 is a schematic diagram of a circuit for use in the infrared detectors of the present invention; and FIG. 5 is a schematic diagram of a tilting filter for use in the ultraviolet detection of $NO_x$.

DESCRIPTION OF THE PREFERRED EMBODIMENTS

Figure 1:
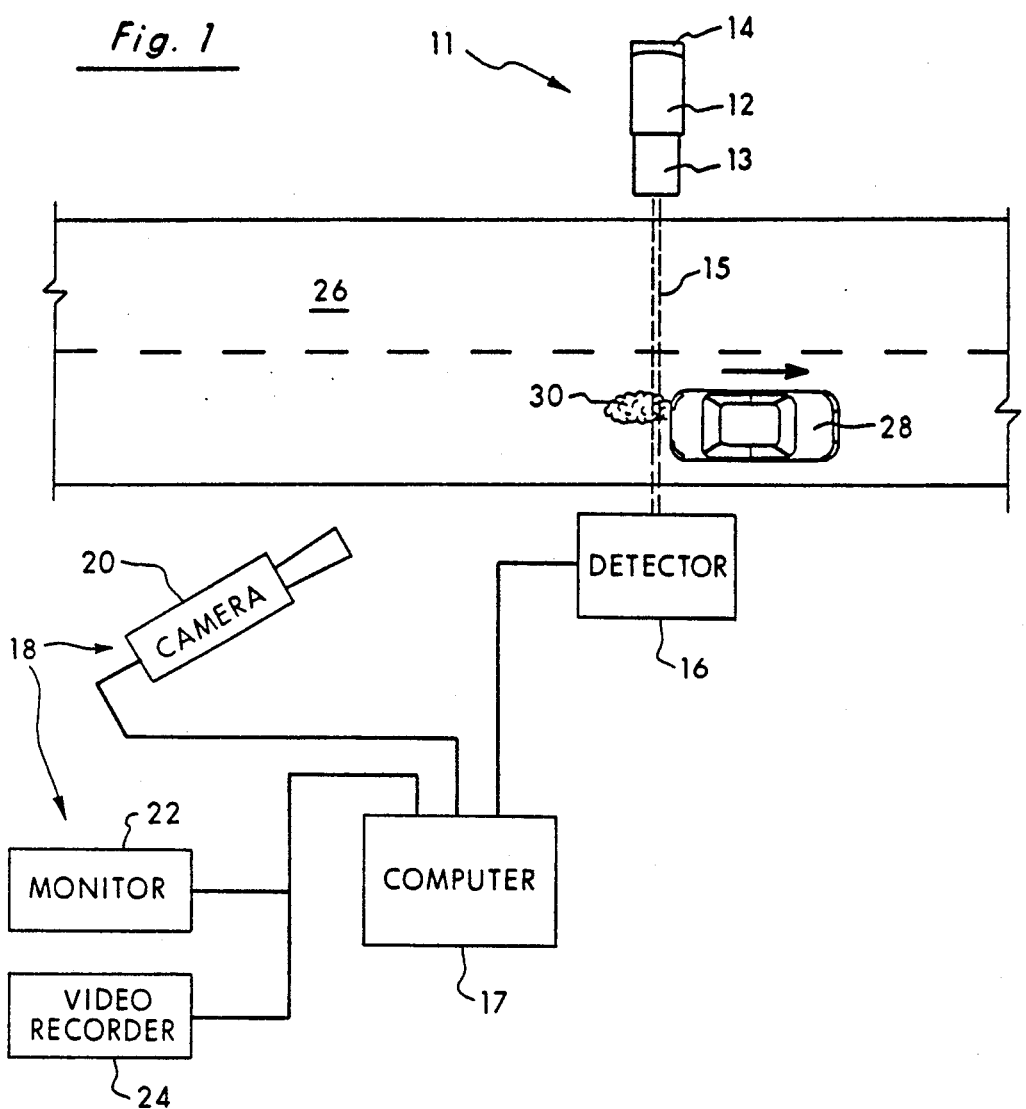
FIG. 1 is a schematic diagram of the remote measuring and monitoring system of the present invention shown in use across a roadway with one vehicle and its exhaust in a detection position.

Referring now to FIG. 1, the system of the present invention includes four basic components. The system 10 includes a light source 11, made up of an ultraviolet radiation source 12, an infrared radiation source 13, a device 14 for collimating the light beams from the sources 12 and 13 into a collimated beam 15, a detector unit 16, a computer 17, and a video monitoring system 18. The video monitoring system 18 preferably includes a video camera 20, a monitor unit 22 and a video recording storage device 24. Of course, ultraviolet radiation source 12 and/or infrared radiation source 13 may be collimated, and therefore not require collimating device 14.

The present invention utilizes infrared absorption to determine the amounts of carbon monoxide, carbon dioxide, hydrocarbons and water added to the air by an individual passing vehicle as well as utilizing ultraviolet absorption to determine the amounts of nitrogen oxides added to the air by such a vehicle. The light source 11 is located on one side of an open space, typically a roadway 26, along which a vehicle 28 moves. The light source 11 sends a collimated beam of radiation 15 into the detector unit 16 on a continuous basis. Across the road reference beams for both the infrared wavelengths and the ultraviolet wavelengths are also developed by the detector unit 16. A computer system 17, including a memory, continuously samples all infrared and ultraviolet beam intensities received by detector 16. When the beam 15 is blocked by a vehicle 28, as it passes along the roadway 26, the memory of computer 17 retains information concerning the carbon monoxide, carbon dioxide, hydrocarbon, nitrogen oxide and water levels in the atmosphere in front of vehicle 28, prior to the blocking of beam 15, and then samples the carbon monoxide, carbon dioxide, hydrocarbon, nitrogen oxide and water levels of exhaust 30 behind vehicle 28 for from about 0.1 to about 1.0 second after resumption of reception of the beam 15 by detector 16.

In one preferred embodiment, a vehicle identifying system, such as video camera 20, records the end view portion of vehicle 28 simultaneous with the unblocking of the beam 15 by the vehicle 28, including the license plate displayed thereby. This is generally the rear portion of the vehicle 28, although the front or other portions of the vehicle may be recorded. When the vehicle 28 has passed the detector 16 and the exhaust 30 has been sampled, the results are compared to the carbon monoxide, carbon dioxide, hydrocarbon, nitrogen oxide and water levels recorded prior to beam interruption, as well as to calibration plots stored in computer memory. The carbon monoxide, carbon dioxide, hydrocarbon, nitrogen oxide and water emission levels are then displayed on the monitor 22 along with a stop-frame video image of the vehicle 28 in relation to the date and time of the emissions measurement. This is then permanently stored in memory or media by unit 24. Any type of storage unit 24 may be utilized with the invention including digital image storage and the like. Thus, the carbon monoxide, carbon dioxide, hydrocarbon, nitrogen oxide and water emissions of the vehicle 28 are remotely sensed, and an identifying image of the vehicle, say a stop-frame video, is overlaid by the date, time, the number of the vehicle in a series of vehicles (if desired), and the various emission levels, while also simultaneously permitting real-time reading of the data at the monitor 22. The computer system 17 may be designed to actually read the vehicle license plate using currently available optical character recognition software, or the operator of the system 10 may read the information from monitor 22 and then physically enter it and the license plate number into the computer data base. Then, if the computer 17 or associated equipment is on-line with the Department of Motor Vehicle License Registration data bank, the vehicle type, model and year can also be displayed on the video image, along with the mandatory, if any, emission requirements of the state. In this manner, a particular vehicle could be identified as complying or non-complying with state emission requirements immediately at the time and site of measurement, or at a later time if desired.

In more particular reference to FIG. 1 and one preferred embodiment of the invention, any available ultraviolet and infrared radiation source may be utilized with the present invention, along with a mechanism for directing the radiation source or beam 15 across the roadway 26. In the present invention, a preferred infrared radiation source includes a commercial gas dryer ignitor, General Electric number WE4X444. A preferred ultraviolet radiation source includes a xenon arc lamp 12 emitting ultraviolet radiation therefrom. One manner of directing the infrared and ultraviolet radiation beams from the sources 12 and 13, respectively, includes the use of a reflective mirror 14 to direct the collimated beam of infrared radiation from the infrared source 13 across the roadway 26. A dichroic mirror or prism is provided in front of mirror 14 through which ultraviolet radiation from the ultraviolet source 12 passes so as to blend with the infrared radiation beam to form a combined collimated beam 15. Another preferred embodiment of the present invention includes the use of a narrow angle CaF prism, with the sources 12 and 13 positioned at appropriate angular alignments to the prism so that a combined collimated beam 15 is emitted therefrom. With such a prism, the infrared radiation is hardly bent when passing therethrough, although the ultraviolet is bent at a considerable angle. The appropriate arrangement of the sources 12, 13 relative to such a prism (not illustrated) would enable the ultraviolet beam to be exactly combined with the infrared beam in the collimated beam 15.

Figure 2:
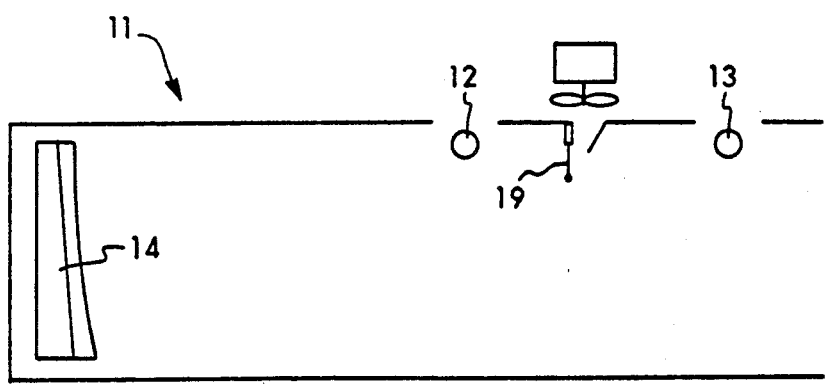
FIG. 2 is a schematic diagram of one preferred embodiment of a light source for use in the remote measuring and monitoring system of the present invention.

A second, and more preferred embodiment of the present invention is illustrated in FIG. 2, which illustrates the use of a dichroic mirror 19, which reflects ultra violet radiation and passes infrared radiation.

With more particular reference to FIG. 3 and one preferred embodiment of the detector unit 16, an opening area 32 is provided for receiving the collimated beam 15. The opening area 32 is arranged such that as the collimated beam 15 enters therethrough, it is focused onto an adjustable mirror 34 onto a beam splitter 38, say one composed of CaF and appropriate overcoatings which allow it to function as a beam splitter. While not shown, a CaF prism may also be utilized in order to divide the collimated beam 15 into two beams, one ultraviolet beam 40 and one infrared beam 42. As previously indicated, using a CaF narrow angle prism, infrared is hardly bent while the ultraviolet is bent at a considerable angle. Thus, the not shown prism, functions as a beam splitter to divide the ultraviolet and infrared portions from the collimated beam 15. The ultraviolet beam 40 is directed to an ultraviolet photomultiplier device 44 which functions to measure the absorption of ultraviolet in the roadway 26 exterior to the device 16.

In the illustrated embodiment, an additional beam splitter 46 is provided to divide the ultraviolet beam 40 into two components, one component 48 being directed onto the photomultiplier 44 while another component 50 is directed onto a device 51 useful for measuring background radiation. In one preferred form, a tilting interference filter 52, (which as seen in FIG. 5) is mounted at an angle on a rapidly rotating shaft, is employed to generate a DC electrical signal in the absence of NO, but provides an AC electrical signal in the presence of NO. With AC coupled electronics, only the NO is observed by the photomultiplier unit 44. The photomultiplier unit 44 is designed to provide a first electrical signal indicative of the absorption of ultraviolet radiation from the collimated beam 15 in the area 26.

Now, with more particular reference to FIGS. 2 and 3, the detector unit 16, with an opening area 32 is provided which observes across a road 26 across which is transmitted beam of infrared radiation and ultraviolet radiation in a single beam 15. Beam 15 is created using two separate light sources, infrared radiation from source 13 and ultraviolet radiation from source 12. The infrared and ultraviolet radiation are combined into the single beam 15 by dichroic mirror 19. Dichroic mirror 19 is overcoated for ultraviolet radiation reflection, and passes infrared radiation, thereby passing infrared radiation and reflecting ultraviolet radiation. In the detector, the beam is split into ultraviolet radiation and infrared radiation by a substantially identical dichroic mirror 38 and the ultraviolet radiation is then detected with an appropriate interference filter 52 and photomultiplier tube 44, as described above.

In this embodiment, the infrared beam 42 continues through the device 16 and is focused onto a polygon structure 27, in this case a dodecagon which has a light and infrared radiation reflective mirror 29 covering each of its sides. The beams 42 to the focusing mirrors reflected from mirrors 29 of polygon 27 are in turn directed through a plurality of filters 37 at a wavelength of 3.9 microns for the reference, 4.3 for $CO_2$, 4.6 for CO, 3.3 for HC, and 2.8 for $H_2O$ mounted upon a multiplicity of infrared detectors 35 (as seen in FIG. 4), in a manner such that each filter passes the wavelength indicative of HC, $CO_2$ and CO, with one detector serving as a reference. For example, a liquid nitrogen cooled, indium antimonide photovoltaic detector or a lead selenide detector operated at or below ambient temperature can be used for each of the infrared detectors 35.

Referring back to the ultraviolet beam 40 and the photomultiplier unit 44, $NO_x$, preferably NO, is measured by making use of the ultraviolet absorption in the wave length range of about 230 nm. The use of ultraviolet absorption for NO has several advantages. These advantages include a ultraviolet absorption coefficient of about 1000 times larger than an infrared absorption coefficient, giving rise to larger signals. Moreover, there is no interference from water vapor in the ultraviolet. The atmosphere is optically transparent, but ultraviolet radiation from the sun is irrelevant because the stratospheric ozone layer cuts out all the ultraviolet radiation. Finally, solar-blind ultraviolet detecting photomultiplier tubes as utilized in the unit 44, are available which are very sensitive and stable. This means that very low, i.e. eye safe, levels of ultraviolet radiation can be used for detection in the unit 16.

In operation, the detector 16 is set up preferably along a single-lane highway with the collimated ultraviolet and infrared beam 15 located approximately 10 inches above the roadway. The computer 17 monitors the infra-red and ultraviolet signal intensities of the reference channel, and the signals are optimize by alignment of the source 11 and the detector unit 16. Upon entry of a vehicle 28 into the optical path of the beam 15, a drop in the reference voltage signals the presence of the vehicle 28. Voltages from each of the signal channels (i.e., the NO detector 44 signal, the CO, the $CO_2$, the HC, the $H_2O$, and the reference detectors 35 signals) that were acquired prior to the vehicle 28 interrupting the beam 15 are stored by the computer 17. While the vehicle 28 continues to block the beam, zero correction voltages for each channel are acquired. As the vehicle 28 exits the beam 15 so that the beam 15 is again received by the detector 16 (from about 0.1 to about 1 second) voltage versus time data streams from each of the channels are acquired by the computer 17. A data stream time train of from about 0.1 to about 1.0 second is a preferred selected time, chosen for convenience. The signals received are averaged over from about 1 millisecond to about 20 milliseconds, with about 10 milliseconds being preferred. By thus averaging the signal a better signal to noise ratio is obtained. Emission results are obtained by computing the ratios of the NO, CO, $CO_2$, and HC voltages (I) to the reference voltages ($I_o$) and rescaling these arbitrary units into calibrated NO, CO, $CO_2$, HC and $H_2O$ values with the use of calibration curves determined in a laboratory utilizing special flow cells with controlled mixtures of NO, CO, $CO_2$, HC and $H_2O$. Those data are then analyzed by the computer 17 by a least squares procedure to determine the path independent $CO/CO_2$ ratio as well as the other desired ratios.

A visual recording device, such as a video camera 20 of any desired make or manufacture is preferably positioned along the roadway 26 spaced from the detector 16 and oriented so as to focus on the area between the detector 16 and the light source 11. The camera 20 is directly linked to the computer 17 such that as a vehicle 28 interrupts the beam 15, the camera 20 is activated so as to record the end, preferably rear, of the vehicle 28 including the license plate thereof. A visual monitor 22 is linked to the computer 17 and the camera 20 so as to provide on-line visual identification of the vehicle 28 for remote location, while a video recording device 24 of any desired type is utilized to provide a permanent record of what is displayed on the monitor 22. While the display on the monitor 22 provides a picture of the rear of the vehicle 28, the computer 17, upon determining the NO, CO, $CO_2$, HC and $H_2O$ levels, displays that information on the monitor display simultaneously with the viewing of the rear of the vehicle 28 so that the information is overlaid onto the picture of the vehicle 28. In addition, the video image of the vehicle is further overlaid by the date and time of the emissions recording so as to provide a permanent record for the particular vehicle 28. Furthermore, the computer 17 may have on-line access to the Department of Motor Vehicle Registrations so that it can also further provide the video display with the make, model, and year of the vehicle 28 based on the license plate information recorded so as to provide real-time determination as to emissions compliance or non-compliance with any state regulations of a particular make, model and year vehicle.

As can be seen from the above, the present invention provides a unique system for the remote measuring and monitoring of emissions from moving motor vehicles. In particular, the present invention provides for a device which will simultaneously measure CO, $CO_2$, HC, NO and/or $H_2O$ depending on a desired measurement. This particular invention allows a remote sensing and measuring so that vehicles do not have to be stopped and can be spot-checked at any given time. Moreover, this particular system permits the visual display as well as permanent recording of such display of the actual vehicle, including license plate identification which is displayed in conjunction with the exhaust measurements. Such a system could be utilized to enforce complete emission standards under real use real use conditions and/or to simply obtain real-time measurements so as to permit vehicle owners to be made aware of necessary corrections of vehicle emissions. The capability of measuring nitrogen oxide and hydrocarbon levels is particularly useful, since there is presently no existing system available which allows such measurements, and such measurements are crucial to the whole emission picture of any given vehicle. The unique capability of measuring NO, HC in conjunction with CO and $CO_2$, as well as identifying by license plate number, the specific vehicle responsible for such emissions for both immediate and future use is exceptionally beneficial, both from an emissions enforcement aspect as well as environmental aspects to permit the actual owner and operator of the vehicle to be aware of real-time use emissions of the vehicle.

The adaption of the system for the measurement of the amount of water vapor present in the exhaust provides an indication of the exhaust system temperature. The amount of water vapor serves as an indication of whether the vehicle was recently started (cold) or warmed up. Cold engines tend to generate substantially more pollutants than warm engines, and also to produce water droplets rather than vapor as would an engine operating above 100° C. A one to one molar ratio of water vapor to CO and $CO_2$ would indicate a warm engine, while a smaller ratio would indicate a cold engine. By measuring the amount of water vapor as compared to CO and $CO_2$ it could be determined whether an engine was running dirty because of it was cold or because the vehicle emission systems were malfunctioning. abundantly clear that the system of the present invention may also be easily adapted to measure the opacity the exhaust of a vehicle, and thereby provide an indication of the nongaseous particulate matter being generated by the vehicle engine.

Currently contemplated state of the art modifications include the incorporation of both the infrared and ultraviolet radiation source and the detector system in a single or in side by side units on the same side of roadway 26. In such an instance the source sends the beam out through a beam splitter to, for example, commercially available retroreflectors which serve to return the beam to the same beam splitter, which directs the split beam to the detector unit for processing as detailed above.

It is therefore seen that the present invention provides an improved remote gas analysis device for the detecting, measuring and recording of emission levels of substantially all gaseous components in the exhaust, such as $NO_x$, CO, $CO_2$, HC and $H_2O$, of in use vehicles. It also simultaneously measures the temperature of the vehicle exhaust while also measuring the amount of specific gaseous pollutants. The system, as described, also includes, in one embodiment, a visual recording device for recording the vehicle and test results.

While the invention has been particularly shown, described and illustrated in detail with reference to preferred embodiments and modifications thereof, it should be understood by those skilled in the art that the foregoing and other modifications are exemplary only, and that equivalent changes in form and detail may be made therein without departing from the true spirit and scope of the invention as claimed, except as precluded by the prior art.

The embodiments of the invention in which an exclusive property or privilege is claimed are defined as follows:

1. A gas analysis device for detecting and measuring levels of gases in the exhaust of moving motor vehicles in the ambient atmosphere selected from the group consisting of carbon monoxide, carbon dioxide, hydrocarbons, nitrogen oxides and water vapor levels, said device comprising:
   a. source means for producing collimated infrared and ultraviolet radiation and transmitting such radiation through a portion of said motor vehicle exhaust;
   b. means for splitting said infrared and ultra-violet radiation into separate infrared and ultraviolet beams;
   c. means for receiving said ultraviolet beam and generating a first electrical signal indicative of the absorption of ultraviolet radiation by nitrogen oxides in said exhaust;
   d. means for splitting said infrared beam into at least two separate infrared beam components;
   e. means for receiving a first infrared beam component and generating a second electrical signal indicative of the absorption of said infrared beam by carbon dioxide in said exhaust;
   f. means for receiving a second infrared beam component and generating at least a third electrical signal therefrom indicative of the absorption of said infrared beam by gases in said exhaust selected from the group consisting of carbon monoxide, hydrocarbons and water vapor; and
   g. means responsive to said electrical signals for computing and producing output signals indicative of the amount of gases selected from the group consisting of carbon monoxide, hydrocarbons and water in the path of said collimated infrared and ultraviolet radiation in said exhaust.

2. The device as claimed in claim 1, wherein said infrared beam splitting means further includes means for splitting said beam into a third infrared beam component, and wherein said device further includes means for receiving said third infrared beam component and generating a fourth electrical signal indicative of the absorption of said infrared beam by a fourth gas selected from the group consisting of carbon monoxide, hydrocarbons and water vapor, said electrical signal responsive means further including means responsive to said fourth electrical signal for computing and producing an output signal indicative of the amount of said fourth gas in the path of said collimated beam in said exhaust.

3. The device as claimed in claim 1, wherein said infrared beam splitting means further includes means for splitting said beam into a third infrared beam component, and wherein said device further includes means for receiving said third infrared beam component and generating a fourth electrical signal indicative of the absorption of said infrared beam by a fourth gas selected from the group consisting of carbon monoxide, hydrocarbons and water vapor, said electrical signal responsive means further including means responsive to said fourth electrical signal for computing and producing an output signal indicative of the amount of said fourth gas in the path of said collimated beam in said exhaust.

4. The device as claimed in claim 1, wherein said infrared beam component detection means is selected from the group consisting of liquid nitrogen cooled, indium antimonide photovoltaic detector units and lead selenide detector units operated at or below ambient temperature.

5. The device as claimed in claim 1, wherein said ultraviolet beam detection means comprises an ultraviolet photomultiplier.

6. The device as claimed in claim 1, wherein said device includes means for splitting said ultraviolet beam into an ultraviolet detection beam and an ultraviolet reference beam.

7. The device as claimed in claim 1, wherein said means for splitting said infrared beam and said ultra-violet beam includes a dichroic beamsplitter constructed to bend the ultraviolet beam at a considerable angle relative to bending of the infrared beam, thereby separating said infrared and ultraviolet beams.

8. The device as claimed in claim 1, wherein said means for splitting said infrared beam and said ultra-violet beam includes a calcium fluoride beamsplitter constructed to reflect the ultraviolet beam at a considerable angle relative to the transmission of the infrared beam, thereby separating said infrared and ultraviolet beams.

9. The device as claimed in claim 1, wherein said means for splitting said infrared beam into at least two separate infrared beam components comprises a rotation polygonal structure having a mirror on each side, whereby the infrared beam is directed sequentially onto at least two separate infrared detector systems.

10. A gas analysis system for the remote sensing, measuring and recording of carbon monoxide, carbon dioxide, hydrocarbons, nitrogen oxide and water vapor levels in the exhaust of moving motor vehicles, said system comprising;
   a. means for generating and directing a collimated beam of infrared and ultraviolet radiation across an open space of sufficient size to permit passage of moving vehicles therethrough;
   b. detector means for receiving said collimated infrared and ultraviolet beam and producing in response thereto a first electrical signal indicative of the absorption of said beam radiation by nitrogen oxides, a second electrical signal indicative of the absorption of said beam radiation by carbon monoxide, a third electrical signal indicative of the absorption of said beam radiation by carbon dioxide, a fourth electrical signal indicative of the absorption of said beam radiation by hydrocarbons, a fifth electrical signal indicative of the absorption of said beam radiation by water, and a sixth electrical signal indicative of the total absorption of said beam radiation in said open space between said beam generating means and said detection means, said beam generating means and said detector means being aligned at a elevation such that a moving vehicles passing through such open space interrupts reception of said collimated beam by said detector means by blocking said beam;

c. means responsive to said electrical signals for computing and producing output signals indicative of the amount of nitrogen oxides, carbon monoxide, carbon dioxide and hydrocarbons in the path of said collimated beam in said open space;

d. memory storage means for storing said output and signal information prior to beam interruption;

e. means for sampling said electrical signals and corresponding output signals for from about 0.1 to about 1.0 second after resumption of collimated beam reception by said detector means; and f. means for correlating and comparing said output signals before and after beam interruption to determine any increase of nitrogen oxides, carbon monoxide, carbon dioxide, hydrocarbons and water vapor levels in the open space due to the exhaust of the moving vehicle responsible for beam interruption as well as for calculating and providing ratios of all tested species to carbon dioxide for the exhaust of said vehicles.

11. The system as claimed in claim 10, wherein said detection means includes means for measuring the background infrared and ultraviolet radiation levels in the said open space for providing reference calibration signals to monitor the total infrared and ultraviolet beam intensities for comparison with said electrical signals generated by said computing means to provide said output signals.

12. The system as claimed in claim 10, wherein said detection means includes a prism for splitting said infrared and ultraviolet radiation into two separate beams within said detection means, an infrared beam splitter means for dividing said infrared beam into four separate infrared beam paths within said detection means, a ultraviolet detection unit aligned to receive said ultraviolet beam, and four separate infrared detection units aligned to receive said four infrared beam paths, each said infrared detection unit including a band pass filter member to isolate, respectively, carbon monoxide, carbon dioxide, hydrocarbons and water spectral regions from said split beam paths to provide said second, third, fourth and fifth electrical signals.

13. The system as claimed in claim 10, wherein said system further includes computing means including a memory for continuously sampling all infrared and ultraviolet beam intensities received by said detector means and includes means for computing the ratios of the carbon monoxide, carbon dioxide, hydrocarbons, nitrogen oxide and water voltages to reference voltages and rescaling these units into calibrated carbon monoxide, carbon dioxide, hydrocarbons, nitrogen oxide and water values data.

14. The system as claimed in claim 13, wherein said computing means further includes means for analyzing said values to determine the path independent $CO/CO_2$ ratio as well as the other $gas/CO_2$ ratios.

15. The system as claimed in claim 10, wherein said system further includes means positioned along said open space, spaced from said detector means and orientated for visually recording for identification the end portion of a moving vehicle as it passes through said open space and interrupts the reception of said collimated beam by said detector means; means for visually monitoring the output of said visually recording means while simultaneously displaying said nitrogen oxide, carbon monoxide, carbon dioxide, hydrocarbons and water level information available from said correlation means in conjunction with the exhaust of the same moving motor vehicle; and means for storing the information displayed on said monitor means.

16. The system as claimed in 15, wherein said visual recording means comprises a video camera aligned to record the end portion of said moving vehicle, including any vehicle identification material displayed on said moving vehicle, as said vehicle interrupts the reception of said collimated beam by said detector means.

17. The system as claimed in claim 15, wherein said monitoring means includes a visual monitor device connected to said correlation means to display the output of said video camera simultaneously with the output of said correlation means to provide on line information of levels in the exhaust of the identified vehicle.

18. The system as claimed in claim 17, wherein said storing means comprises a video recording device to store the display of said monitor device.

* * * * *